(12) United States Patent
Fefer

(10) Patent No.: US 6,673,360 B2
(45) Date of Patent: Jan. 6, 2004

(54) TECHNIQUE FOR EMULSIFYING HIGHLY SATURATED HYDROISOMERIZED FLUIDS

(75) Inventor: Michael Fefer, Whitby (CA)

(73) Assignees: Platte Chemical Company, Greeley, CO (US); Petro Canada, Alberta ( * ) Notice: Subject to any disclaimer, the term of this patent is extended or adjusted under 35 U.S.C. 154(b) by 0 days.

(21) Appl. No.: 10/354,936

(22) Filed: Jan. 29, 2003

(65) Prior Publication Data

US 2003/0187079 A1 Oct. 2, 2003

Related U.S. Application Data

(62) Division of application No. 09/783,497, filed on Feb. 13, 2001, now Pat. No. 6,515,031.

(51) Int. Cl.⁷ .......................... A01N 25/04; A01N 27/00
(52) U.S. Cl. ....................... 424/405; 514/546; 514/668; 514/762; 514/786; 514/941; 504/363; 516/73
(58) Field of Search .................... 516/73, 918; 504/103, 504/363; 514/786, 546, 668, 762, 941; 71/64.08; 424/403, 405

(56) References Cited

U.S. PATENT DOCUMENTS

| | | | | |
|---|---|---|---|---|
| 2,162,904 A | | 6/1939 | Allison ........................ | 514/762 |
| 2,167,144 A | * | 7/1939 | Barton et al. .................. | 516/73 |
| 2,246,230 A | * | 6/1941 | Yates .......................... | 514/762 |
| 2,264,762 A | * | 12/1941 | Knight ........................ | 514/786 |
| 3,227,609 A | * | 1/1966 | Wilson, Jr. et al. .......... | 514/762 |
| 3,624,019 A | * | 11/1971 | Anderson et al. ......... | 252/363.5 |
| 3,804,830 A | * | 4/1974 | Landsdorf, Jr. ............. | 540/494 |
| 4,822,407 A | * | 4/1989 | Esposito ..................... | 504/130 |
| 5,358,988 A | * | 10/1994 | Schieferstein et al. ...... | 524/280 |
| 5,554,315 A | * | 9/1996 | Tonomura et al. ............ | 516/75 |
| 5,580,567 A | * | 12/1996 | Roberts ........................ | 516/53 |
| 5,589,515 A | * | 12/1996 | Suzuki et al. .................. | 516/73 |
| 5,693,258 A | * | 12/1997 | Tonomura et al. ........... | 516/918 |
| 6,255,253 B1 | * | 7/2001 | Foerster et al. ............. | 504/363 |
| 6,515,031 B2 | * | 2/2003 | Fefer ........................... | 516/73 |

OTHER PUBLICATIONS

Nita A. Davidson, et al., "Managing Insects and Mites with Spray Oils", University of California, Division of Agriculture and Natural Resources, Publication 3347, 1991, pp. 5–14, month unknown.

"Material Safety Data Sheet, SPRAY OIL 10E, 13E, 15E, 22E", Petro–Canada, Oct. 16, 2000.

"RHODASURF L–4", Material Safety Data Sheet, Rhodia Canada, Inc., Jun. 4, 1999.

"ALKAMULS GMR–55–LG", Material Safety Data Sheet, Rhodia Canada Inc., Apr. 16, 1998.

"The HLB System", Chapters 1–3, ICI Surfactants, on or before Dec. 5, 2000.

McCutcheon's vol. 1: Emulsifiers & Detergents North American Edition 1993 (McCutcheon Division, MC Publishing Co., Glen Rock NJ, USA copyright 1993) p. 87, Jan. 1994.

* cited by examiner

*Primary Examiner*—Daniel S. Metzmaier
(74) *Attorney, Agent, or Firm*—Hogan & Hartson L.L.P.

(57) ABSTRACT

A preferred emulsifier blend includes ethoxylated alcohols containing hydrocarbons of C10–C16 and preferably having on average at least 2.8 ethoxy and/or alcohol groups per chain and a glycerol mono- and/or dioleates, preferably in a ratio of from 9:1 to 4:6. These emulsion blends are particularly useful when mixed with hydroisomerized oils and water, for subsequent application as a spray oil to agricultural crops. The emulsion blends of the present invention also find particular utility when mixed with conventional spray oils and hard water.

5 Claims, No Drawings

TECHNIQUE FOR EMULSIFYING HIGHLY SATURATED HYDROISOMERIZED FLUIDS

RELATED APPLICATION

The present application is a divisional application of U.S. patent application Ser. No. 09/783,497, filed Feb. 13, 2001, now U.S. Pat. No. 6,515,031, which is incorporated by reference herein in its entirety.

FIELD OF THE INVENTION

The present invention relates emulsifiers for highly saturated, hydrocracked and/or hydroisomerized fluids. More particularly, the present invention relates to compositions containing emulsified, highly saturated hydrocracked, and/or hydroisomerized oils particular useful when applied to crops.

BACKGROUND OF THE INVENTION

Petroleum oils have long been sprayed on agricultural crops as a means of pest control. Properly processed petroleum oils are generally less phytotoxic than many synthetic pesticides, with the resulting oil cover affecting the target mites, flies, bugs, scales, aphids and the like but having little deleterious effect on the target tree, plant or crop.

Conventional spray oils are manufactured from crude oil and petroleum fractions using conventional solvent refining techniques or using hydro-treated base oils. Typically, the higher the paraffinic content (i.e., the proportion of saturated straight or branched hydrocarbon chains) in the oil, the more effective the oil is against pests and the less phytotoxic it is to plants. Oils containing high normal paraffinic contents can lead to an elevated pour temperature, which can cause problems when the oil is applied as a spray oil in colder climates.

Finished spray oils typically include 1 to 3 weight percent (wt %) of an emulsifier to allow the oil to remain emulsified in a water carrier during spraying. Conventional emulsifiers for this purpose include alkyl phenol ethoxylates.

Although such alkyl phenol ethoxylates perform satisfactorily under most conditions, their emulsification capability decreases substantially under hard water conditions. When conventional spray oils emulsified with alkyl phenol ethoxylates and hard water, separation can occur during or shortly after spraying, in which case the non-emulsified oil or other composition constituents separate out on the plant leaf, causing phytotoxicity which may be evidenced by leaf browning.

Severely hydrocracked and/or severely hydrocracked hydroisomerized oils, having a saturate content of ≧99% and/or exhibiting a high degree of branching of the paraffin molecules, are now available. Exemplary severely hydrocracked and hydroisomerized oils include the Spray Oil 10, Spray Oil 13, Spray Oil 15 and Spray Oil 22 hydrocracked and hyroisomerized oils available from Petro-Canada Lubricants of Mississauga, Ontario L5K 1A8, Canada, characteristics of which are summarized below:

| Quality | Test Method | Spray Oil 1 | Spray Oil 13 | Spray Oil 15 | Spray Oil 22 |
| --- | --- | --- | --- | --- | --- |
| Appearance | Visual | clear bright | clear bright | clear bright | clear bright |
| Color | ASTM D1500 | <0.5 | <0.5 | <0.5 | <0.5 |
| Density @ 15° C. | ASTM D1298 | 0.83 kg/l | 0.84 kg/l | 0.84 kg/l | 0.84 kg/l |
| Viscosity @ 40° C. | ASTM D445 | 9.5 cSt | 20.0 cSt | 20.0 cSt | 20.0 cSt |
| Analine Point | ASTM D611 | 103 | 113 | 113 | 113 |
| Nitrogen | ASTM D4629 | <1 ppm | <1 ppm | <1 ppm | <1 ppm |
| Sulphur | ASTM D5453 | <1 ppm | <1 ppm | <1 ppm | <1 ppm |
| Saturates | PCM 528 | >99.9 wt % | >99.9 wt % | >99.9 wt % | >99.9 wt % |
| Aromatics | PCM 528 | <0.1 wt % | 0.1 wt % | 0.1 wt % | 0.1 wt % |
| Polynuclear aromatics | HRMS | <1 ppm | <1 ppm | <1 ppm | <1 ppm |

The hydrotreating or hydrocracking step can be carried out in the presence of a catalyst based group VIB and VIII metals, or alternatively, in the presence of a catalyst based on a crystalline silicoaluminophosphate molecular sieve. Typical hydrocracking or hydrotreating conditions include temperatures of from 200 to 450° C., hydrogen pressures of from 400 to 5,000 psig, a hydrogen circulation rate of 400 to 15,000 SCF/B and space velocities of from 0.1 to 20 hr-1. Hydroisomerization is typically carried out after the hydrocracking or hydrotreating step using a crystalline silicoaluminophosphate molecular sieve catalyst, which optionally contains group VIII and IIA metals. The process is carried out at a temperature of from 250 to 450° C., at hydrogen pressures of from 100 to 5000 psig, a hydrogen circulation rate of 400 to 15,000 SCF/B and liquid hourly space velocity of 0.1 to 20 hr-1. The hydroisomerized fluid is hydrofinished at temperatures of from 190 to 340° C. and pressures of from 400 to 500 psig, a hydrogen circulation rate of 400 to 15,000 SCF/B, in the presence of a solid metal hydrogenation catalyst. The initial hydrotreating or hydrocracking step can be carried out in the presence of a catalyst based group VIB and VIII metals, or alternatively, in the presence of a catalyst based on a crystalline silicoaluminophosphate molecular sieve. Typical hydrocracking or hydrotreating conditions include temperatures of from 200 to 450° C., hydrogen pressures of from 400 to 5,000 psig, a hydrogen circulation rate of 400 to 15,000 SCF/B and space velocities of from 0.1 to 20 hr-1. Typically, the finished product has a natural pour point of from −30 to −60° C., and below, with a preferred pour point of below −50° C.

While the above techniques are used to produce severely hydrocracked and hydroisomerized fluids, issues of adequate emulsification performance under hard water conditions present with such fluids can also be present with fluids which are not hydroisomerized but are hydrocracked or obtained through solvent extraction and contain 80–95 wt % or more saturates. As used herein the phrase hydrocracked and/or hydroisomerized fluids includes organic fluids which are either hydrocracked or hydroisomerized or both and contain a saturate content of >80%. Examples of such fluids available from suppliers other than Petro-Canada are described below:

| Quality | Test Method | Exxon 100N | Chevron 100R | SunSpray 11N |
| --- | --- | --- | --- | --- |
| Appearance | Visual | clear/bright | clear/bright | clear/bright |
| Color | ASTM D1500 | <0.5 | <0.5 | <0.5 |

-continued

| Quality | Test Method | Exxon 100N | Chevron 100R | SunSpray 11N |
|---|---|---|---|---|
| Density @ 15° C. | ASTM D1298 | 0.8639 | 0.8551 | 0.857 |
| Viscosity @ 40° C. | ASTM D445 | 20.24 | 20.52 | 19.28 |
| Analine Point | ASTM D611 | 97.6 | 106.4 | 101.9 |
| Saturates | PCM 528 | 81.2 | 95.6 | 93.0 |
| Aromatics | PCM 528 | 18.8 | 4.4 | 7.0 |
| Polynuclear aromatics | HRMS | 5.8 | 1.2 | 1.7 |

Unfortunately, hydrocracked and/or hydroisomerized fluids are not readily usable as spray oils because they are often less soluble then conventional oils. As a result of this poorer solubility, the otherwise conventional alkyl phenol emulsifiers tend to drop out of solution upon standing. Conventionally used emulsifiers do not seem to perform adequately and do not have the required storage stability when added to hydrocracking and/or hydroisomerized oils.

The emulsification capability of a potential emulsifier may be evaluated by considering its hydrophile/lipophile balance (hereinafter HLB value). The HLB value, which is an approximate measure of polarity, usually ranges from 2–18. The higher the number, the more polar the subject molecule—the lower the number, the less polar the subject molecule. The more polar molecules are generally more soluble in water and the less polar molecules generally more soluble in oil. However, in evaluating potential emulsifiers for use with hydroisomerized fluids, the HLB values have proven to have poor predictive value, with no single emulsifier performing satisfactorily.

Below is a list of commercially available emulsifiers, which were tested for emulsification ability with hydrocracking and hydroisomerized fluids, including emulsifier class, source, product name, HLB value, average number of ethoxylate or alcohol groups per molecule, and carbon chain numbers, if known.

| emulsifier class | source | product name | HLB | # EO/ OH | C Chain |
|---|---|---|---|---|---|
| ethoxylated alcohol | De-forest[1] | Delonic LF-EP-18 | 6.0 | | |
| | | Delonic LF-EP-20 | 6.2 | | |
| | | Delonic LF-EP-25 | 7.0 | | |
| | | Delonic LF-EP-30 | 8.0 | | |
| ethoxylated alcohol | Shell[2] | Neodol 23-3 | 7.9 | 2.9 | C12-C13 |
| | | Neodol-23-1 | 3.7 | 1 | C12-C13 |
| | | Neodol 25-3 | 7.5 | 2.8 | C12-C13; C14-C15 |
| | | Neodol 1-3 | 8.7 | 3 | C11 |
| sorbitan monooleate | ICI[3] | SPAN 80 | 4.3 | | |
| ethoxylated alcohol | | Synperonic A4 | 9.1 | 4 | C13-C15 |
| | | Synperonic A3 | 7.9 | 3 | C13-C15 |
| polyoxyethylene lauryl ether | | Brij 30 | 9.7 | 4 | C16-C18 |
| | | Brij 93 | 4.9 | 2 | |

| emulsifier class | source | product name | HLB | # EO/ OH | C Chain |
|---|---|---|---|---|---|
| ethoxylated alcohol | De-forest[1] | Delonic LF-EP-18 | 6.0 | | |
| | | Delonic LF-EP-20 | 6.2 | | |
| | | Delonic LF-EP-25 | 7.0 | | |
| | | Delonic LF-EP-30 | 8.0 | | |
| ethoxylated alcohol | Shell[2] | Neodol 23-3 | 7.9 | 2.9 | C12-C13 |
| | | Neodol-23-1 | 7.9 | 2.9 | C12-C13 |
| | | Neodol 25-3 | 3.7 | 3.7 | C12-C13; C14-C15 |
| sorbitan monooleate | ICI[3] | Neodol 1-3 | 8.7 | 8.7 | C11 |
| | | SPAN 80 | 4.3 | | |
| ethoxylated alcohol | | Synperonic A4 | 9.1 | 4 | C13-C15 |
| | | Synperonic A3 | 7.9 | 3 | C13-C15 |
| polyoxyethylene lauryl ether | | Brij 30 | 9.7 | 4 | |
| | | Brij 93 | 4.9 | 2 | |

None of these emulsifiers alone provided satisfactory emulsification with Spray Oil 22 and Spray Oil 10 hydrocracked and hydroisomerized fluids.

It can be see there remains a continuing need for an emulsifier that can emulsify hydrocracked and/or hydroisomerized fluids. There remains a further need for such an emulsifier for use with hydrocracked and/or hydroisomerized fluids, which will result in an emulsified product which is satisfactory for use in agricultural applications as a spray oil. In addition, there remains a need for an emulsifier adaptable for use with conventional spray oils as well as hydroisomerized spray oils, that will maintain emulsification ability when solubilized in hard water, so as to minimize phytotoxicity to the plants to which such spray oils are applied. It is against this background that the techniques of the present invention have been developed.

SUMMARY OF THE INVENTION

The emulsifier blends of the present invention include ethoxylated alcohols containing C10–C16 carbon chains having on average 2.8 or more ethoxy or alcohol groups per carbon chain together with glycerol mono-, di- and/or tri-oleates. A preferred emulsifier blend of the present invention contains ethoxylated alcohol:glycol mono- and/or dioleates in a ratio of wt % of from 9:1 to 4:6. Said another way, a preferred emulsifier blend of the present invention contains from 90% to 40% by weight of ethoxylated alcohols and 10% to 60% of a mixture of glycol mono and/or dioleates. A more preferred emulsifier blend contains C12–C16 carbon chains and contains ethoxylated alcohols and glycerol mono- and/or dioleates in a ratio of 9:1 to about 6:4. A most preferred ratio of ethoxylated alcohols and glycerol mono- and/or dioleates is 4:1.

The emulsifier blends of the present invention find particular utility in the emulsification of hydrocracked and/or hydroisomerized fluids, especially oils, which may then be employed as spray oils for subsequent application to agricultural crops. The emulsifier blends of the present invention are also very useful in emulsifying conventional spray oils in hard water, prior to application to agricultural crops.

DETAILED DESCRIPTION

The emulsifier blends of the present invention include ethoxylated alcohols containing C10–C16 carbon chains having on average at 2.8 or more ethoxy or alcohol groups per carbon chain together with glycerol mono- and/or dioleates. A preferred emulsifier blend of the present invention contains ethoxylated alcohol:glycol mono- and/or dioleates in a ratio of wt % of from 9:1 to 4:6. Said another way, a preferred emulsifier blend of the present invention contains from 90% to 40% by weight of ethoxylated alcohols and 10% to 60% of a mixture of glycol mono and/or dioleates. A more preferred emulsifier blend contains C12–C16 carbon chains and contains ethoxylated alcohols and glycerol mono- and/or dioleates in a ratio of 9:1 to about 6:4. A most preferred ratio of ethoxylated alcohols and glycerol mono- and/or dioleates is 4:1.

The process of evaluating and identifying a preferred ethoxylated alcohol/glycerol dioleate composition is further described below in Example I.

EXAMPLE I

As summarized in Table I below, 0.5 grams of each ethoxylated alcohol product was weighed and added, with mixing, at room temperature, to a beaker containing 50 grams of the Spray Oil 10 hydrocracked and hydroisomerized oil. Added to the oil was 0.3 grams of a rapeseed mono- and diglyceride product obtained from Rhodia Canada, Inc. under the tradename Alkamuls GMR-55-LG, with mixing. When difficulty in solubilizing occurred or turbidity occurred, the preparation was warmed slightly. The oil/emulsifier blend was set aside for 12–24 hours to confirm no additional separation had occurred. To quantify emulsifier performance, 1 ml of the oil/emulsifier blend was added to a 100 ml graduated cylinder of water. The graduated cylinder was then plugged with a stopper, inverted 10 times to allow proper distribution of the oil. The stopper was then removed and a timer started. The timer was stopped when 1 ml of fluid had separated to form a top oil layer. Product performance was characterized as poor (1 ml top layer in <45 seconds), good (1 ml layer in ≧45 seconds but <90 seconds), and excellent (1 ml layer in ≧90 seconds). Performance is summarized in Table I.

TABLE I

| ethoxylated alcohol product | amount | HLB | # EO | hydro-carbon chain | Time to 1 ml separation | performance |
|---|---|---|---|---|---|---|
| Synperonic A2 | 0.5 gm | 5.9 | 2 | C13-C15 | 10 sec | poor |
| Synperonic A3 | 0.5 gm | 7.9 | 3 | C13-C15 | 45 sec | good |
| Synperonic A4 | 0.5 gm | 9.1 | 4 | C13-C15 | 95 sec | excellent |
| Rhodasurf L-4 | 0.5 gm | 9.7 | 4 | C10-C16 | 251 sec | excellent |
| Brij 93 | 0.5 gm | 4.9 | 2 | | 15 sec | poor |
| Renex 30 | 0.5 gm | 14.5 | 12 | C30 ether | 27 sec | poor |

It can be seen that an emulsifier blends of the present invention containing an ethoxylated alcohol comprising primarily C10–C16 hydrocarbon chains with an average of 3 or more ethoxylate or alcohol groups, in combination with glycerol mono- and/or dioleates, satisfactorily emulsifies the Spray Oil 10 product tested.

EXAMPLE II

To a beaker containing 50 grams of Spray Oil 10 hydrocracked and hydroisomerized oil was added 1.0 grams of Rhodasurf L-4 ethoxylated alcohol along with a listed amount of Alkamuls GMR-55-LG mono/diglyercide product. 1 ml of each such oil/emulsifier blend was then added to a 100 ml graduated cylinder of water which was plugged with a stopper and inverted 10 times. The stopper was removed and a timer started. The timer was stopped when 1 ml of fluid had separated to form a top layer. Product performance was characterized as above and summarized in Table II.

TABLE II

| ethoxylated alcohol | amount | HLB | No. EO | hydro-C chain | glycol dioleate | Time to 1 ml separ. | performance |
|---|---|---|---|---|---|---|---|
| Rhodasurf L-4 | 1 gm | 9.1 | 4 | C10-C16 | 0.0 gm | 22 | poor |
| Rhodasurf L-4 | 0.9 gm | 9.1 | 4 | C10-C16 | 0.1 gm | 63 | good |
| Rhodasurf L-4 | 0.8 gm | 9.1 | 4 | C10-C16 | 0.2 gm | 148 | excellent |
| Rhodasurf L-4 | 0.7 gm | 9.1 | 4 | C10-C16 | 0.3 gm | 55 | good |
| Rhodasurf L-4 | 0.6 gm | 9.1 | 4 | C10-C16 | 0.4 gm | 85 | good |
| Rhodasurf L-4 | 0.5 gm | 9.1 | 4 | C10-C16 | 0.5 gm | 48 | good |
| Rhodasurf L-4 | 0.4 gm | 9.1 | 4 | C10-C16 | 0.6 gm | 51 | good |
| Rhodasurf L-4 | 0.3 gm | 9.1 | 4 | C10-C16 | 0.7 gm | 13 | poor |
| Rhodasurf L-4 | 0.2 gm | 9.1 | 4 | C10-C16 | 0.8 gml | 18 | poor |
| Rhodasurf L-4 | none | 9.1 | 4 | C10-C16 | 1.0 ml | 11 | poor |

Based on these results, a preferred emulsifier blend of the present invention contains ethoxylated alcohol:glycol mono- and/or dioleate in a ratio of wt % from 9:1 to 4:6. Said another way, a preferred emulsifier blend of the present invention contains from 90% to 40% by weight of ethoxylated alcohols and 10% to 60% of a mixture of glycol mono and/or dioleates. A more preferred emulsifier blend contains C12–C16 carbon chains. A more preferred emulsifier blend also contains ethoxylated alcohols and glycerol mono- and/or dioleates in a ratio of 9:1 to about 6:4. A most preferred ratio of ethoxylated alcohols and glycerol mono- and/or dioleates is 4:1.

EXAMPLE III

To a beaker containing 100 grams of Spray Oil 22™ hydrocracked and hydroisomerized oil was added 1.4 grams of one of the various Neodol ethoxylated alcohol products available from Shell Oil Co., plus 0.06 gm Alkamuls GMR-55-LG mono/diglyercide product. 1 ml of each such oil/emulsifier blend was then added to a 100 ml graduated cylinder of water which was plugged with a stopper and inverted 10 times. The stopper was removed and a timer started. The timer was stopped when 1 ml of fluid had separated to form a top layer. Product performance was characterized as above and summarized in Table III.

TABLE III

| ethoxylated alcohol | HLB | # EO | hydro-C chain | Time to 1 ml separation | performance |
|---|---|---|---|---|---|
| Neodol 91-6 | 12.4 | 6 | C9/C10, C11 | 6 | poor |
| Neodol 91-2.5 | 8.5 | 2.7 | C9/C10, C11 | 20 | poor |
| Neodol 1-5 | 11.2 | 5 | C11 | 22 | poor |
| Neodol 23-1 | 3.7 | 1 | C12/C13 | 23 | poor |
| Neodol 25-3 | 7.5 | 2.8 | C12/C13 C14/C15 | 90 | excellent |
| Neodol 1-3 | 8.7 | 3 | C11 | 98 | excellent |
| Neodol 23-6.5 | 12.0 | 6.6 | C12/C13 | 131 | excellent |

The above example demonstrates that the preferred ethoxylated alcohols contain predominantly hydrocarbon chains of length C11 or more, most preferably C12/C13 hydrocarbon chains, and contain on average at least 2.8 ethoxylate groups per chain.

EXAMPLE IV

To test the emulsifier blend of the present invention with the Exxon 100N, Chevron 100R and SunSpray 11N hydrocracked and/or hydroisomerized oils described above, a beaker containing 100 grams of each oil was mixed with either 1.6 grams of TMulzA02 ("known emulsifier") or 1.12 grams of Rhodasurf L-4 plus 0.48 grams Alkamuls GMR-55-LG mono/diglyercide product ("new emulsifier"). 1 ml of each such oil/emulsifier blend was then added to a 100 ml graduated cylinder of water which was plugged with a stopper and inverted 10 times. The stopper was removed and a timer started. The timer was stopped when 1 ml of fluid had separated to form a top layer. Product performance was characterized as above and summarized in Table IV.

TABLE IV

| Base oil | | Time to 1 ml separation | performance |
|---|---|---|---|
| Exxon 100N | new emulsifier | 173 | excellent |
| Exxon 100N | known emulsifier | 390 | excellent |
| Chevron 100R | new emulsifier | 85 | good |
| Chevron 100R | known emulsifier | 53 | good |
| SunSpray 11N | new emulsifier | 535 | excellent |
| SunSpray 11N | known emulsifier | 35 | poor |

It can be seen that use of an emulsifier blend of the present invention with each of the above-listed base oils resulted in product performance which was either good or excellent. In addition, it can be seen that base oil performance improved for both the Chevron 100R and SunSpray 11N products when used with an emulsifier blend of the present invention.

EXAMPLE V

In what resulted in further unexpected results, an emulsion blend of the present invention was able to emulsify a standard spray oil in hard water substantially better than a conventional emulsifier added to the spray oil. More particularly, an emulsion blend of the present invention containing 70 wt % of Rhodasurf L4 was mixed with 30 wt % of the Alkamuls® GMR-55/LG glycerol mono and dioleate product described above along with 50 grams standard Spray Oil 10, a severely hydrocracked and hydroisomerized neutral base oil with additives, available from Petro-Canada of Calgary, Alberta, Canada. One ml of this oil/emulsion blend was then added to 100 ml. of water obtained from 17 different sites in California. Water from each these locations can be characterized as hard water, as is apparent from the measured mineral content of a water sample from each of these sites, summarized in Table V(a) below.

TABLE V(a)

| Site | Mineral Content of Water in ppm | | | | |
|---|---|---|---|---|---|
| No. | B | Ca | Si | Mg | Zn |
| 1. | 1.7 | 10.1 | 7.3 | 0.7 | — |
| 2. | 1.4 | 31.5 | 8.9 | 4.8 | — |
| 3. | 1.4 | 26.7 | 8.4 | 0.2 | — |
| 4. | 1.1 | 7.4 | 5.2 | 0.2 | — |
| 5. | 1.2 | 27.2 | 7.0 | 3.0 | — |
| 6. | 1.1 | 51.5 | 6.9 | 5.3 | — |
| 7. | 1.3 | 38.8 | 9.2 | 3.6 | — |
| 8. | 1.0 | 30.5 | 5.5 | 2.7 | — |
| 9. | 1.4 | 15.7 | 4.1 | 9.1 | — |
| 10. | 1.0 | 2.9 | 1.7 | 0.4 | — |
| 11. | 1.4 | 52.7 | 11.6 | 2.9 | — |
| 12. | 1.1 | 32.0 | 10.8 | 29.4 | — |
| 13. | 1.2 | 36.9 | 9.6 | 8.0 | — |
| 14. | 0.5 | 116 | 4.3 | 38.6 | 1.1 |
| 15. | 1.9 | 4.8 | 5.3 | 0.5 | 0.5 |
| 16. | 1.8 | 4.6 | 5.0 | 0.5 | — |
| 17. | 2.0 | 4.9 | 5.7 | 0.5 | 0.5 |

Emulsification performance was timed as described as above in Examples I and II, with the time required for a 1 ml top layer to separate listed below in Table V(b). Emulsion performance was then compared in each case with emulsion performance of the Spray Oil 10 when combined with the listed wt % of TMulz A02 FS02, a conventional emulsifier available form Harcros Chemicals, Inc. The separation times for these products, in minutes, to emulsion separation for each sample are also listed Table V(b).

TABLE V(b)

| | Emulsifier Blend | | | | Emulsifier TMulz A02 FS02 | | | | |
|---|---|---|---|---|---|---|---|---|---|
| | 1.0 wt % | 1.2 wt % | 1.4 wt % | 1.6 wt % | 1.0 wt % | 1.2 wt % | 1.4 wt % | 1.6 wt % | 1.8 wt % |
| Site No. | Emusifier performance in minutes to form separated 1 ml layer | | | | | | | | |
| 1. | >7 | >7 | >8 | >8 | <2 | <2 | <1 | <2 | <2 |
| 2. | >8 | >9 | >10 | >8 | <1 | <1 | <1 | <1 | < |
| 3. | >5 | >6 | >5 | >7 | <1 | <1 | <1 | <1 | <1 |
| 4. | >10 | >6 | >4 | >2 | <1 | <1 | <1 | <1 | <1 |
| 5. | >10 | >7 | >11 | >15 | <1 | <1 | <1 | <1 | <1 |
| 6. | >8 | >8 | >12 | >15 | <1 | <1 | <1 | <1 | <1 |
| 7. | >3 | >4 | >14 | >23 | <1 | <1 | <1 | <1 | <1 |
| 8. | >6 | >7 | >11 | >14 | <1 | <1 | <1 | <1 | <1 |
| 9. | >8 | >8 | >10 | >13 | <1 | <1 | <1 | <1 | <1 |
| 10. | >9 | >11 | >16 | >18 | <1 | <1 | <1 | <1 | <2 |
| 11. | >3 | >3 | >4 | =7 | <1 | <1 | <1 | <1 | <1 |
| 12. | >4 | >9 | >12 | >8 | <1 | <1 | <1 | <1 | <1 |
| 13. | >29 | >36 | >41 | >48 | <1 | <1 | <1 | <1 | <1 |
| 14. | >2 | >5 | >5 | >7 | <1 | <1 | <1 | <2 | <2 |
| 15. | >21 | >27 | >40 | >62 | <2 | <2 | <2 | <2 | <2 |
| 16. | >6 | >9 | >16 | >22 | <1 | <1 | <1 | <1 | <1 |
| 17. | >3 | >3 | >6 | >12 | <1 | <1 | <1 | <1 | <1 |

As is readily apparent from a review of the data, the emulsifier blend of the present invention maintained oil emulsification in all cases except one, for over 3 minutes, and many substantially over 3 minutes. In contrast, all of the tests using a convention emulsifier separated in less than 2 minutes, with over 85% of the samples separating in less than 1 minute.

Spray Oil Functionality

Phytotoxicity generally relates to injury to plants arising from application of exogenous substances to plants. Such substances can include fertilizers, herbicides and other types of compounds applied to plant soil or to plant surfaces, such as by foliar spraying. Many substances have a safe application rates, at which phytotoxicity is non-existent or de minimus, but can injure or kill plants at higher application rates. Other compounds are per se phytotoxic. As a general rule, when applied as a physical barrier to treat pest infestation, lighter spray oils have less potential for phytotoxicity then equivalent but heavier spray oils, but are often less effective for pest control than equivalent heavier spray oils. In order to increase pest control effectiveness of the lighter spray oils, greater application rates are sometimes employed, but this approach too can result in increased phytotoxicity. As further discussed below, a decrease in phytotoxicity has been achieved by use of the emulsifier of the present invention, when used with higher application rates of both lighter and heavier highly hydroisomerized spray oils.

EXAMPLE VI

Spray oils were evaluated for phytotoxicity and for certain disease-control factors in a grove of 11-year-old Ruby Red grapefruit (Citrus paradisi) on Swingle citrumelo (Poncirus trifoliata x C. sinensis) rootstock near Lake Alfred, Fla. Each treatment was applied to five two-tree plots arranged in completely randomized design. Ten shoots per tree from the spring flush of growth were tagged in April 1999. All products were applied to foliage from June 29 to Jul. 1, 1999 using a handgun sprayer at 200 psi. The rate per acre indicated in the table was added to 125 gallons and the trees were sprayed using about three gallons per tree. An application of ethion was made on Jul. 9, 1999 to control rust mite.

TABLE VI

| Treatment Description | Applic. rate/acre | Phytotox rating |
|---|---|---|
| Control | None | 0.00 |
| Spray Oil 15 + new emulsifier | 10 gal | 1.12 |
| Spray Oil 15 + known emulsifier | 10 gal | 1.08 |
| Spray Oil 22 + new emulsifier | 10 gal | 1.03 |
| Spray Oil 22 + known emulsifier | 10 gal | 1.12 |
| Spray Oil 15 + new emulsifier | 15 gal | 1.06 |
| Spray Oil 15 + known emulsifier | 15 gal | 1.43 |
| Spray Oil 22 + new emulsifier | 15 gal | 1.00 |
| Spray Oil 22 + known emulsifier | 15 gal | 1.40 |
| Sunspray oil (455) + known emulsifier | 10 gal | 0.97 |
| Sunspray oil (455) + known emulsifier | 15 gal | 1.34 |

Phytotoxicity symptoms were noted on leaves on the spring flush of growth. Most oil sprays produced a raised blister type of symptom which had a superficial resemblance to greasy spot, but no chlorosis was associated with these symptoms. Of the Petro-Canada oils, there was no difference between the phytotoxicity rating for Spray Oil 15, rated at 1.17 and Spray Oil 22, rated at 1.14. The average rating for Sunspray 455 was 1.16.

However, the average for the treatments with the conventional emulsifier was significantly higher than the treatments with the new emulsifier (1.26 as compared to 1.05) and this was especially evident at the 15-gallon rate. No defoliation was associated with the leaf damage caused by the oils.

Bearing in mind that the Petro-Canada oil and Sunspray oil treatments may be preferred for pest control over traditional "chemical" insecticide treatments like the BASF 500-00F 2.07 EC, traditional metal treatments like the copper-based Kocide 2000 product, and traditional fungicides like Flint 50, with the heavier weight oils and heavier application preferred, the reduction in phytotoxicity at a 15 gallon application rate for Spray Oil 22 and Spray Oil 15 by substitution of the known emulsifier with the new emulsifier of the present invention is significant. More particularly, the reduction in phytotoxicity with a gallon per acre application of Spray Oil 15 from 1.43 to 1.06 when utilizing the emulsion of the present invention and the similar reduction in phytotoxicity with a 15 gallon per acre application Spray Oil 22 from 1.40 to 1.00 is significant.

With respect to the disease control factors, all of the fungicides tested significantly reduced the severity of greasy spot on the spring flush. The petroleum spray oil treatments controlled greasy spot, but response differed with the various oils. The average severity rating for the 10-gallon rates for all oils, 0.05, and the average rating for the 15-gallon rate, 0.14, were not significantly different. Most of the oil treatments were as effective as the standard copper treatment.

EXAMPLE VII

Spray oils were evaluated for defoliation and marketable fruit yields—both an aspect of phytotoxicity—and for certain disease-control factors, in the grove of 10-year-old Ruby Red grapefruit described above. Each treatment was applied to five two-tree plots arranged in randomized complete block design. Ten shoots per tree from the spring flush of growth were tagged in April 1998. All products were applied to foliage from Jul. 7 to 9, 1998 using a handgun sprayer at 200 psi. The rate per acre indicated below was added to 125 gallons and the trees were sprayed using about 3 gallons per tree.

TABLE VII

| Treatment Description | Application rate/acre | % Defoliation | % Marketable Fruit |
|---|---|---|---|
| Control | None | 10.1 | 67.3 |
| Spray Oil 13 w/new emulsifier | 10 gal | 4.4 | 73.3 |
| Spray Oil 13 w/new emulsifier | 20 gal | 5.4 | 48.0 |
| Spray Oil 15 + new emulsifier | 10 gal | 4.4 | 73.3 |
| Spray Oil 15 + known emulsifier | 10 gal | 7.9 | 58.0 |
| Spray Oil 15 + new emulsifier | 20 gal | 4.3 | 90.7 |
| Spray Oil 15 + known emulsifier | 20 gal | 4.9 | 68.0 |
| Spray Oil 22 + new emulsifier | 10 gal | 2.1 | 85.3 |
| Spray Oil 22 + known emulsifier | 10 gal | 8.7 | 86.7 |
| Spray Oil 22 + new emulsifier | 20 gal | 5.3 | 83.3 |
| Spray Oil 22 + known emulsifier | 20 gal | 3.8 | 90.7 |
| Sunspray 435 oil | 10 gal | 5.3 | 86.0 |

When Spray Oils 13, 15 and 22 are compared at 10 and 20 gallon application rates across all of the different formulations, the 20-gal rate increased the percentage of marketable fruit compared to the 10-gal rate. In addition, the addition of the emulsifier of the present invention to Spray Oils 13 and 15 markedly increased the percentage of marketable fruit as compared to the use of the known emulsifier when combined with these same spray oils.

EXAMPLE VIII

Spray oils were evaluated for phytotoxicity to fruit and leaves in citrus—with the tests conducted on California oranges. Treatments in quarts/acre of various oil/emulsifier compositions were tested in a range of water concentrations. Phytotoxicity of leaves and fruit were measured at various intervals, with phytotoxicity of leaves and fruit summarized below in Table VIII, as measured on Sep. 2, 1999 (mid-season), with phytotoxicity of fruit also measured just prior to harvest (Dec. 29, 1999).

TABLE VIII

| Treatment Description | Applicat'n rate per acre | Water per acre | Sept. 2, 1999 phytoxicity leaves | Sept. 2, 1999 phytoxicity fruit | Dec. 29, 1999 phytoxicity fruit |
|---|---|---|---|---|---|
| Control | None | none | 0.0 | 0.0 | 0.0 |
| Spray Oil 10 new emulsifier | 72 qt | 1500 gal | 1.3 | 2.0 | 0.7 |
| Spray Oil 13 new emulsifier | 72 qt | 1500 gal | 2.0 | 2.0 | 0.0 |
| Spray Oil 22 new emuisifier | 72 qt | 1500 gal | 3.0 | 3.0 | 0.0 |
| Spray Oil 10 new emulsifier | 72 qt | 750 gal | 1.3 | 2.0 | 0.0 |
| Spray Oil 13 new emulsifier | 72 qt | 750 gal | 2.0 | 2.0 | 0.0 |
| Spray Oil 22 new emulsifier | 72 qt | 750 gal | 2.7 | 2.7 | 0.0 |
| Spray Oil 10 new emulsifier | 72 qt | 250 gal | 2.0 | 2.0 | 0.0 |
| Spray Oil 13 new emulsifier | 72 qt | 250 gal | 3.0 | 1.7 | 0.0 |
| Spray Oil 22 new emulsifier | 72 qt | 250 gal | 3.0 | 3.0 | 0.0 |
| Exxon 796 conven emulsifier | 72 qt | 1500 gal | 3.0 | 3.0 | 0.0 |
| Exxon 796 conven emulsifier | 72 qt | 750 gal | 2.3 | 2.0 | 0.0 |
| Exxon 796 conven emulsifier | 72 qt | 250 gal | 4.0 | 3.0 | 2.0 |
| Spray Oil 13 new emulsifier | 144 qt | 1500 gal | 3.7 | 3.0 | 4.0 |
| Spray Oil 13 new emulsifier | 144 qt | 250 gal | 4.0 | 4.7 | 3.7 |
| Exxon 796 conven emulsifier | 144 qt | 1500 gal | 4.0 | 5.0 | 4.0 |
| Exxon 796 conven emulsifier | 144 qt | 250 gal | 4.3 | 6.0 | 4.0 |

Referring now to Table VIII, it can be seen that application of hydroisomerized oils with the emulsions of the present invention generally resulted in lowered mid-season leaf phytotoxicity than spray oils mixed with a conventional emulsifier. Moreover, at the 72 quart per acre application rate, the hydroisomerized oils in combination with an emulsion of the present invention had no appreciable fruit phytotoxicity just prior to harvest, with the 144 quart per acre application rate exhibiting fruit phytotoxicity at rates similar to that of the Exxon 796 product.

EXAMPLE IX

Spray oils were evaluated for effectiveness in achieving early control of citrus rust mite populations in grapefruit groves in Lake Alfred, Fla. In each case, control plots were maintained to track when the natural growth and subsidence of the rust mite population, it being understood that if the natural growth of the rust mite population is allowed to occur, damage to marketable fruit quality and/or yield will probably have occurred, making it important to accelerate the decline of the rust mite population in advance of the natural subsidence. Spray Oils 10, 13, 15 and 22 emulsified with an emulsifier composition of the present invention, which was applied to 10 year old trees at 10 or 15 gallons/acre rates with a Durant Wayland PTO-driven speed sprayer calibrated for 125 gallons/acre. The treated trees were compared with untreated control trees and with trees sprayed with a standard spray oil emulsified with T-Mulz. Rust mite infestion was rated prior to application and at identified intervals post application. Results are summarized below in Table IX.

TABLE X

| Treatment Description | Application rate/acre | 3 days prior to treatment | 6 days post treatment | 12 days post treatment | 25 days post treatment |
|---|---|---|---|---|---|
| Control | None | 19.38 | 46.49 | 48.97 | 9.66 |
| Spray Oil 22 | 10 gal | 35.82 | 0.05 | 0.02 | 0.06 |
| Spray Oil 22 | 15 gal | 13.41 | 0.55 | 0.13 | 0.03 |
| Spray Oil 15 | 10 gal | 19.51 | 0.52 | 0.08 | 0.00 |
| Spray Oil 15 | 15 gal | 19.26 | 1.11 | 0.15 | 0.15 |
| Spray Oil 13 | 10 gal | 39.28 | 1.28 | 0.63 | 0.13 |
| Spray Oil 13 | 15 gal | 9.55 | 0.25 | 0.31 | 0.03 |

TABLE X-continued

| Treatment Description | Application rate/acre | 3 days prior to treatment | 6 days post treatment | 12 days post treatment | 25 days post treatment |
|---|---|---|---|---|---|
| Spray Oil 10 | 10 gal | 6.66 | 0.53 | 0.20 | 0.08 |
| Spray Oil 10 | 15 gal | 19.41 | 0.44 | 0.04 | 0.03 |
| Conventional spray oil | 10 gal | 16.27 | 2.12 | 0.65 | 0.27 |
| Conventional spray oil | 15 gal | 17.93 | 0.03 | 0.01 | 0.01 |

EXAMPLE X

In the tests below, Spray Oils 13, 15 and 22 emulsified with the emulsifier composition of the present invention, were tested at differing application rates and compared with an untreated control and a standard spray oil emulsified with T-Mulz. A first treatment was made postbloom (in late April) followed by a second treatment in mid-summer (mid-July). Rust mite infestion was rated at mites/cm$^2$ prior to the $2^{nd}$ application, and at identified intervals post $2^{nd}$-application. Results are summarized below in Table X.

TABLE IX

| Treatment Description | Application rate/acre | 19 days prior to $2^{nd}$ treatment | 7 days post $2^{nd}$ treatment | 23 days post $2^{nd}$ treatment | 31 days post $2^{nd}$ treatment |
|---|---|---|---|---|---|
| Control | None | 27.4 | 30.2 | 6.3 | 1.2 |
| Spray Oil 13 | 10 gal | 0.82 | 0.07 | 0.12 | 0.45 |
| Spray Oil 13 | 20 gal | 0.16 | 0.09 | 0.08 | 0.07 |
| Spray Oil 15 | 10 gal | 0.23 | 0.11 | 0.39 | 0.30 |
| Spray Oil 15 | 20 gal | 0.37 | 0.02 | 0.07 | 0.07 |
| Spray Oil 22 | 10 gal | 0.14 | 0.04 | 0.12 | 0.02 |
| Spray Oil 22 | 20 gal | 0.11 | 0.00 | 0.00 | 0.01 |
| Conventional spray oil | 10 gal | 0.15 | 0.31 | 0.15 | 0.17 |
| Conventional spray oil | 20 gal | 0.77 | 0.00 | 0.01 | 0.03 |

EXAMPLE XI

In the tests below, Spray Oils 13, 15 and 22 were mixed to form a composition including (a) 1.2% by weight of emulsifier composition of the present invention, (b) 1.6% by weight of the emulsified composition of the present invention, or (c) 1% by weight of TMulz-A02 (Spray Oil 22 only), and applied with a hand gun at either 10 or 20 gallons per acre, and compared with an untreated control and a standard spray oil emulsified with T-Mulz-A-02. A first treatment was made postbloom (in late April) followed by a second treatment in mid-summer (mid-July) and a third treatment at the end of September. Rust mite infestation was rated at mites/cm$^2$ throughout the season. However, of particular interest are the infestation measurements made just prior to and after the 3$^{rd}$ application, when the rust mite infestation was naturally peaking, as evidenced by the control measurements. Results are summarized below in Table XI.

TABLE XI

| Treatment Description | Application rate/acre | 10 days prior to 3$^{rd}$ treatment | 6 days post 3$^{rd}$ treatment | 14 days post 3$^{rd}$ treatment | 2 days post 3$^{rd}$ treatment |
|---|---|---|---|---|---|
| Control | None | 32.5 | 7.00 | 4.7 | 1.9 |
| Spray Oil 13 (a) | 10 gal | 15.40 | 1.10 | 0.75 | 0.95 |
| Spray Oil 13 (a) | 10 gal | 4.10 | 2.00 | 1.40 | 0.21 |
| Spray Oil 13 (b) | 20 gal | 8.80 | 1.80 | 0.27 | 0.49 |
| Spray Oil 13 (b) | 20 gal | 12.30 | 1.30 | 0.14 | 0.32 |
| Spray Oil 15 (a) | 10 gal | 3.30 | 0.73 | 0.11 | 0.03 |
| Spray Oil 15 (a) | 10 gal | 4.30 | 0.28 | 0.01 | 0.08 |
| Spray Oil 15 (b) | 20 gal | 10.50 | 0.42 | 0.02 | 0.27 |
| Spray Oil 15 (b) | 20 gal | 4.90 | 0.66 | 0.17 | 0.23 |
| Spray Oil 22 (a) | 10 gal | 3.40 | 0.19 | 0.07 | 0.05 |
| Spray Oil 22 (a) | 10 gal | 0.23 | 0.07 | 0.03 | 0.00 |
| Spray Oil 22 (b) | 20 gal | 2.50 | 0.53 | 0.41 | 0.34 |
| Spray Oil 22 (b) | 20 gal | 0.25 | 0.01 | 0.24 | 0.21 |
| Spray Oil 22 (c) | 10 gal | 7.70 | 0.77 | 0.79 | 0.21 |
| Spray Oil 22 (c) | 20 gal | 18.90 | 0.82 | 0.39 | 0.39 |
| Conventional spray oil | 10 gal | 9.90 | 0.14 | 0.11 | 0.07 |
| Conventionai spray oil | 20 gal | 8.30 | 0.13 | 0.00 | 0.09 |

It can be seen that hydroisomerized spray oils, when mixed with an emulsifier composition of the present invention, were effective in accelerating the decline in citrus rust mite population.

Having described the techniques of the present invention, it can now be appreciated that the emulsion blends of the present invention containing ethoxylated alcohols containing primarily hydrocarbons of C10–C16, preferably having on average at least 2.8 ethoxy and/or alcohol groups per chain, together with a glycerol mono- and/or dioleate, in a most preferred ratio of from 9:1 to 4:6. As will be appreciated by those of ordinary skill in the art, while a combination of glycerol mono- and/or dioleates are preferred, glycerol mono-, di- and trioliates may be used alone or in mixtures of varying proportions, The emulsion blends of the present invention are particularly useful when mixed with hydrocracking and/or hydroisomerized oils and water, which may be subsequently employed as a spray oil for agricultural purposes. The emulsion blends of the present invention also find particular utility when mixed with conventional spray oils and hard water.

Reference has been made in detail to presently preferred embodiments of the invention. It is intended that all matter contained in the description above shall be interpreted as illustrative and not in a limiting sense. Moreover, other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A technique for minimizing pest infestations in agricultural acreage comprising:

combining a spray oil with an emulsifier blend, said emulsifier blend comprising: ethoxylated alcohols containing primarily C10–C16 carbon chains with an average of 2.8 or more ethoxy and/or alcohol groups per carbon chain, and glycerol mono- and/or dioleates, wherein the emulsifier blend contains from 90% to 40% by weight of ethoxylated alcohols and from 10% to 60% by weight of the glycerol mono- and/or dioleates;

emulsifying spray oil with the emulsifier blend in water; and spraying the spray oil and emulsifier blend emulsion on the agricultural acreage.

2. The technique for minimizing pest infestations in agricultural acreage of claim 1, wherein the spray oil is a hydrocracked and/or hydroisomerized oil.

3. The technique for minimizing pest infestations in agricultural acreage of claim 1, wherein the hydrocracked and hydroisomerized oil has a saturate content of $\geq 99\%$.

4. The technique for minimizing pest infestations in agricultural acreage of claim 1, wherein the emulsifier blend contains a ratio by weight of ethoxylated alcohols:glycerol mono- and/or dioleates of approximately 4:1.

5. The technique for minimizing pest infestations in agricultural acreage of claim 1 wherein the spray oil and emulsifier blend are combined in a ratio of from about 99:1 to 98:2.

* * * * *